United States Patent [19]
DeVries

[11] Patent Number: 4,596,552
[45] Date of Patent: Jun. 24, 1986

[54] CARDIOPLEGIA CANNULA
[75] Inventor: James H. DeVries, Grand Rapids, Mich.
[73] Assignee: DLP Inc., Grand Rapids, Mich.
[21] Appl. No.: 725,990
[22] Filed: Apr. 22, 1985

Related U.S. Application Data
[63] Continuation of Ser. No. 503,344, Jun. 10, 1983.
[51] Int. Cl.[4] .............................................. A61M 5/00
[52] U.S. Cl. ....................................... 604/44; 604/35; 604/45; 604/118; 604/129; 604/164
[58] Field of Search ....................... 604/44, 22, 27, 35, 604/45, 82, 83, 115, 117–119, 129, 165, 168, 169, 284, 164

[56] References Cited
U.S. PATENT DOCUMENTS
4,016,879  4/1977  Mellor ............................ 604/168
4,202,332  5/1980  Tersteegen et al. ................ 604/284
4,244,365  1/1981  McGill et al. ..................... 604/118
4,280,496  7/1981  Van Baelen ........................ 604/83
4,318,401  3/1982  Zimmerman ....................... 604/284
4,320,761  3/1982  Haddad ............................. 604/22
4,502,502  3/1985  Krug ................................ 604/118

Primary Examiner—Stephen C. Pellegrino
Assistant Examiner—Mark Rooney
Attorney, Agent, or Firm—Barnes, Kisselle, Raisch, Choate, Whittemore & Hulbert

[57] ABSTRACT

An aortic root cannula for use in open heart surgery which combines a luer line for connection with an extracorporeal circuit outside the chest cavity with a left heart vent line and a pressure monitoring line all merging into a base unit having a single cannula for heart wall penetration. A composite base unit is formed of two parts integrated to provide the merging passages to perform the multiple functions.

1 Claim, 6 Drawing Figures

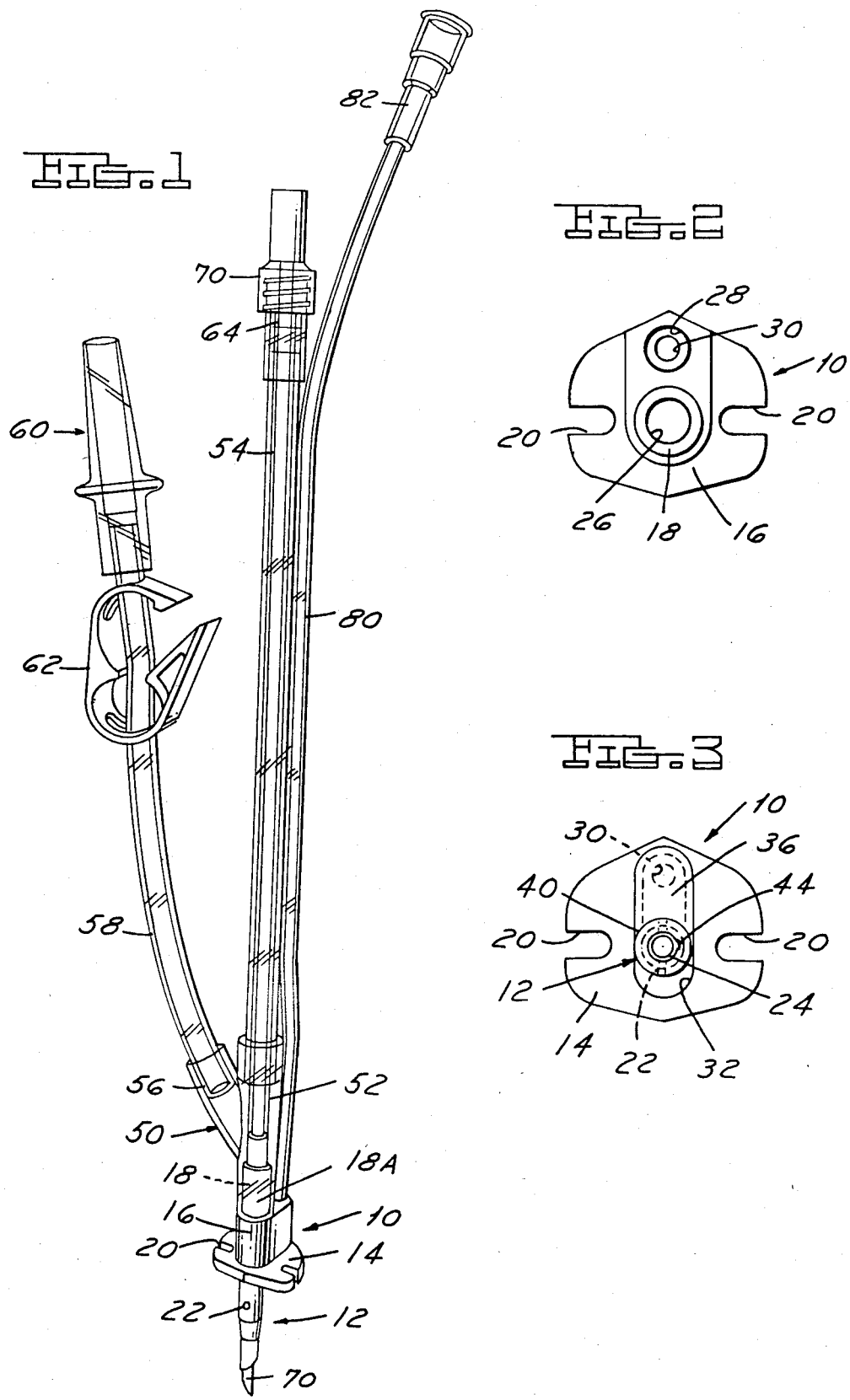

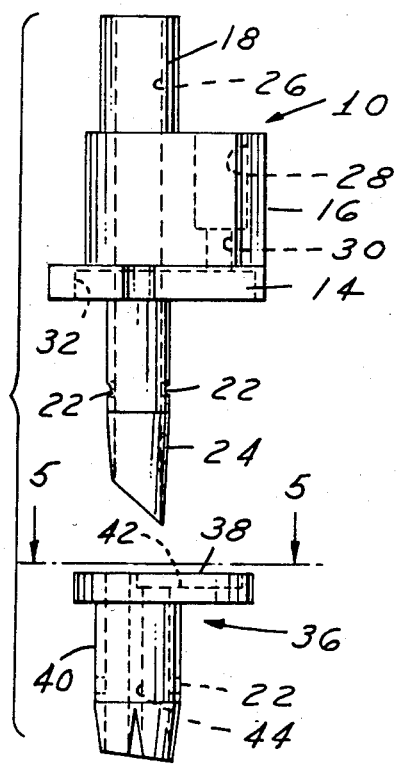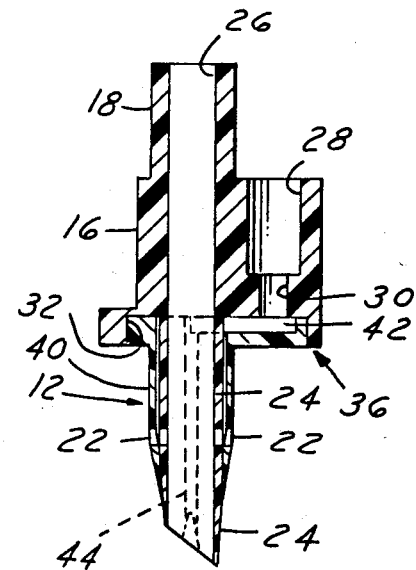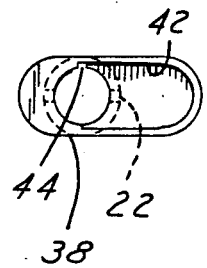

4,596,552

CARDIOPLEGIA CANNULA

REFERENCE TO COPENDING APPLICATION

This application is a continuation of my copending application, Ser. No. 503,344, filed June 10, 1983, entitled "Cardioplegia Cannula".

FIELD OF INVENTION

Open heart surgergy and the use of extracorporeal circuits in which cannula are inserted into the heart for the infusion of cardioplegia solutions.

BACKGROUND OF INVENTION

In open heart surgery, it is common now to insert cannula into the heart to administer a cooled and medicated solution for a function designated as cardioplegia. There are other functions that are also desirable in connection with this type of operation, namely, aspiration of air from the heart chambers, decompression or venting of the heart and monitoring the pressure within the aorta.

It is an object of the present invention to provide a single cannula which can be utilized for a variety of the above functions and thus simplify the accessories leading from extracorporeal equipment to the heart organ itself. The equipment provided is disposable and packaged in sterile condition for immediate use.

Other objects and features of the invention will be apparent in the following description and claims in which the invention is described and details provided to enable a person skilled in the art to make and use the invention, all in connection with the best mode presently contemplated for the invention.

BRIEF DESCRIPTION OF THE DRAWINGS

DRAWINGS accompany the disclosure and the various views thereof may be briefly described as:

FIG. 1, a perspective assembly drawing showing the various elements of the invention.

FIG. 2, a top view of a cannula base unit used in the assembly.

FIG. 3, a bottom view of the cannula base unit.

FIG. 4, an exploded view showing the two parts of the cannula base unit.

FIG. 5, a view on line 5—5 of the top of one element of the cannula.

FIG. 6, a longitudinal sectional view of an assembled cannula base unit.

DETAILED DESCRIPTION OF THE INVENTION AND THE MANNER AND PROCESS OF USING IT

The present disclosure involves a dual purpose cannula which can be used either to infuse cardioplegia solution into the aortic root of the heart organ during open heart surgery or to aspirate air from the aorta. The length must be such that connection to the extracorporeal circuit can be made outside of the chest cavity.

The extracorporeal circuit will include a peristaltic blood pump, temperature controls, aereation to perform the function of the lungs, devices for administering cardioplegic medication, all of which are under the control of the attendant physicians and operating room staff.

In addition to the dual purpose cannula referenced above, it is desirable to accomplish left heart venting and cardioplegic administration without additional penetration of the heart wall.

WITH REFERENCE TO THE DRAWINGS, in FIG. 1, a perspective assembly is illustrated in which a cannula base unit 10 has an insertion tip 12, and a flanged collar 14 above which is body portion 16 and luer connector 18. The flanged collar 14 permits a predetermined insertion depth.

The flange 24 has notches 20 to facilitate the securing of the cannula base unit to the heart with conventional sutures. The flexible insertion tip 12 has symmetrically disposed side holes 22 for use in aspiration. The tip itself is a flexible thin walled structure 24 as illustrated in FIGS. 5 and 6 integral with and projecting from the body 16 and having a canted end.

A main passage 26 (FIGS. 2, 6) extends through the body 16 to the tip 24. A pilot projection 18 at the top end of passage 26 serves to mount the root connection 18A of a Y-connector 50 to be later described. A solvent bond can be used. Adjacent the passage 26 in body 16 is a connection recess 28 with a bottom port 30 opening to an elongate recess 32 in the base of the body 16.

A secondary base element 36, illustrated in isolation in FIGS. 4 and 5, has an elongate flat element 38 with a depending flexible sleeve 40 which surrounds the insertion tip 24 in the area adjacent the body 16. The flat element fits snugly in the recess 32 and a has a top recess 42 which extends over to the sleeve 40. On the inner wall of sleeve 40 is an axial slot 44 extending from the recess 42 to the end of the sleeve 40.

The previously mentioned holes 22 penetrate both the insert tip 24 and the sleeve 40 in a registering relation.

The secondary base element 36 will be cemented or fused into assembly with the main cannula base unit so that the parts become essentially integral.

The connector 18 carries the root 18A or a Y-connector 50 having a main branch 52 with a first female recess to receive the end of a tube 54. The other secondary branch 56, which is conjunctive with the main branch, has a second female recess to receive the end of a tube 58 which carries a connector 60 and a snap-release shut-off valve 62. The distal end of tube 54 has a female luer lock connector 64 which can have a threaded relationship with the distal end of a needle penetrator 70 slidable in tube 54 and readily removable. This female connector with the extended length of tube 54 allows connection to the extracorporeal circuit outside the chest cavity.

The connector 28 receives the proximal end of a small tube 80 which parallels tube 54 and has a connector 82. A solvent or some weld will hold the tube 80 in place. This tube can also be bonded lineally to tube 54.

IN THE OPERATION of the aortic root cannula, the base unit 10 is established on the vessel wall by piercing the wall with the needle end of the penetrator 70 and moving the combined insertion tip 12 composed of portions 24 and 40 through the vessel wall. The notched flanges 14 can be then secured by suitable sutures to the vessel wall and the insertion needle 70 removed from the assembly. With this single insertion, all of the tubes 54, 58 and 80 are connected to the interior of the heart.

Tube 54 is open to the heart through passage 26 in the base unit through the end 24 and the cross-ports 22. The tube 58 is open also to passage 26 through the Y-connector 50. Tube 80 is open through port 30, cross-passage 42 and interior axial slot 44.

Thus, connector 60 on tube 58 can be utilized for a subatmospheric source (suction line) for venting the heart. The tube 54 can be used for the in-flow of cardioplegic liquid and medication, and the samll tube 80 can be used to connect to a pressure monitoring transducer to monitor the pressure in the vessel (aorta) when this is desirable.

The two parts 16 and 36 can be joined by sonic welding or suitable solvent adhesive so that they are essentially integral in use.

I claim:

1. An aortic root cannula for introduction into the heart organ during open heart surgery to selectively administer cardioplegic liquid, permit venting of the heart chamber, and monitor pressure in the heart vessel which comprises:
   (a) a first body element as a base unit having a top and bottom side and a primary cannula extension on the bottom side, a flanged transverse body portion extending to each side of said cannula to form an insertion stop for said cannula, and a main passage entering the top of said first body extending through said body portion and said primary cannula,
   (b) a secondary passage formed in the top of said transverse body portion parallel to and spaced from said main passage and an open sided recess on the bottom of said body portion surrounding said cannula and in communication with said secondary passage,
   (c) a secondary body element secured to the bottom of said first body element received within said open-sided recess to close said recess and having a top surface lying within said recess shaped to permit flow from said secondary passage around said primary cannula, said secondary body having a secondary outer cannula projection fitted over said primary cannula,
   (d) an axially extending passage in one of the surfaces of one of said cannula extending from said recess to the distal end of said cannulae to connect said secondary passage and the area at the end of said cannulae whereby said secondary passage may be connected to a pressure monitoring device,
   (e) a tubular extension affixed to said first body aligned with said main passage for housing a needle penetrator and to be connected to a source of cardioplegic liquid and medication, and an auxiliary connection to said tubular extension also communicating with said main passage to be connected to a subatmospheric source for venting the heart vessel through said cannulae,
   (f) said cannulae also having transverse registering ports open to the exterior of said cannulae.

* * * * *